(12) United States Patent
Sitzman et al.

(10) Patent No.: US 8,805,482 B2
(45) Date of Patent: Aug. 12, 2014

(54) SYSTEM AND METHOD FOR SIGNAL QUALITY INDICATION AND FALSE ALARM REDUCTION IN ECG MONITORING SYSTEMS

(75) Inventors: David A. Sitzman, Hubertus, WI (US); Timothy L. Johnson, Niskayuna, NY (US); Stephen T. Treacy, Milwaukee, WI (US); Sahika Genc, Troy, NY (US)

(73) Assignee: General Electric Conpany, Schenectady, NY (US)

( * ) Notice: Subject to any disclaimer, the term of this patent is extended or adjusted under 35 U.S.C. 154(b) by 1404 days.

(21) Appl. No.: 12/180,616

(22) Filed: Jul. 28, 2008

(65) Prior Publication Data

US 2010/0022903 A1 Jan. 28, 2010

(51) Int. Cl.
*A61B 5/04* (2006.01)

(52) U.S. Cl.
USPC ........................................ 600/509

(58) Field of Classification Search
CPC ............. A61B 5/04017; A61B 5/7217; A61B 5/7221; A61B 5/0402
USPC .......................................... 600/509; 128/901
See application file for complete search history.

(56) References Cited

U.S. PATENT DOCUMENTS

| | | | |
|---|---|---|---|
| 5,085,224 A | 2/1992 | Galen et al. | |
| 5,123,420 A * | 6/1992 | Paret | 600/511 |
| 5,421,342 A | 6/1995 | Mortara | |
| 5,469,856 A | 11/1995 | Lundstrom et al. | |
| 5,490,515 A | 2/1996 | Mortara | |
| 5,520,191 A | 5/1996 | Karlsson et al. | |
| 5,660,184 A | 8/1997 | Donehoo et al. | |
| 5,682,902 A | 11/1997 | Herleikson | |
| 6,117,074 A | 9/2000 | Schurmann et al. | |
| 6,135,952 A | 10/2000 | Coetzee | |
| 6,206,830 B1 | 3/2001 | Diab et al. | |
| 6,266,624 B1 | 7/2001 | Deco et al. | |
| 6,725,074 B1 | 4/2004 | Kastle | |
| 6,801,802 B2 | 10/2004 | Sitzman et al. | |
| 7,079,035 B2 | 7/2006 | Bock et al. | |
| 8,602,986 B2 | 12/2013 | Ali | |
| 2003/0069511 A1 | 4/2003 | Stridh et al. | |
| 2004/0133087 A1 | 7/2004 | Ali et al. | |

FOREIGN PATENT DOCUMENTS

| | | |
|---|---|---|
| DE | 10358397 A1 | 7/2005 |
| EP | 0748637 A2 | 12/1996 |
| GB | 2335747 A | 9/1999 |
| JP | 04231025 A | 8/1992 |
| JP | 08229014 A | 9/1996 |
| JP | 09131330 A | 5/1997 |

(Continued)

OTHER PUBLICATIONS

Clifford, "Signal Processing Methods for Heart Rate Variability," 2002.

(Continued)

*Primary Examiner* — Mark W Bockelman
(74) *Attorney, Agent, or Firm* — Fletcher Yoder, P.C.

(57) ABSTRACT

An electrocardiogram (ECG) monitoring system configured to determine an index that comprises a set of indicators, where each indicator is indicative of a level of signal quality in an ECG lead. Further, the ECG monitoring system assigns a first indicator from the set of indicators to a first ECG lead signal and communicates the first indicator to a user.

20 Claims, 6 Drawing Sheets

(56) References Cited

FOREIGN PATENT DOCUMENTS

| | | |
|---|---|---|
| JP | 09164122 A | 6/1997 |
| JP | 2003505120 A | 2/2003 |
| JP | 2003513693 A | 4/2003 |
| JP | 2007502639 A | 2/2007 |
| WO | 2005/020120 A3 | 3/2005 |
| WO | 2005/070289 A1 | 8/2005 |
| WO | 2005/071600 A1 | 8/2005 |
| WO | 2005/076187 A2 | 8/2005 |
| WO | 2005/101229 A1 | 10/2005 |

OTHER PUBLICATIONS

Henriques et al., "Searching for Similarities in Nearly Periodic Signals With Application to ECG Data Compression," ICPR, 2006.
Zhang, "Wavelet Approach for ECG Baseline Wander Correction and Noise Reduction," IEEE, Sep. 2005, pp. 1212-1215.
Unofficial English translation of Office Action issued in connection with corresponding JP Application No. 2009-170689 on Nov. 19, 2013.
Allen et al., "Assessing ECG Signal Quality on a Coronary Care Unit", Physiological Measurement, vol. 17, pp. 249-258, Nov. 1, 1996.
Farrell et al., Effect of Lead Quality on Computerized ECG Interpretation, Computers in Cardiology, vol. 31, pp. 173-176, Sep. 19, 2004.
Wang, "A New Method for Evaluating ECG Signal Quality for Multi-Lead Arrhythmia Analysis", Computers in Cardiology, vol. 29, pp. 85-88, Sep. 22, 2002.
Search Report dated Feb. 10, 2010.

* cited by examiner

SYSTEM AND METHOD FOR SIGNAL QUALITY INDICATION AND FALSE ALARM REDUCTION IN ECG MONITORING SYSTEMS

BACKGROUND OF THE INVENTION

The invention relates generally to electrocardiogram (ECG) monitoring systems and, more particularly, to determining and indicating the quality of ECG signals.

ECG monitoring systems may be designed to generate alarms indicative of patient medical conditions as well as equipment failure and/or inability to function properly. The ECG monitoring systems may generate "false alarms", which do not result from a medical problem of the patient, but are often based on errors in internal signal processing or from detached or failed leads. False crisis alarms, in particular, waste valuable nursing and emergency staff resources because they may result in an unnecessary rapid response that may divert resources from other patients. Many ECG systems are capable of reliably detecting failed or detached leads, often notifying an operator of the detached or failed leads via an alarm. In addition, many ECG systems provide an indication of a temporary inability to process one or more ECG waveforms. Such an indication is commonly known as an artifact alarm.

Although equipment lead and artifact alarms may have a low priority and often cease when an artifact ends, they can generate display clutter and do not, in general, provide actionable information. Nonetheless, the alarm should still be investigated by monitoring personnel. Additionally, a signal problem often occurs on a channel other than the primary viewing channel, and the default screen shown on a monitor often does not contain information that allows for the identification of which channel the alarm is associated with. Accordingly, an operator often must search for the proper screen to assess the artifact. By the time the proper screen is found, often the problem that initiated the false alarm event has already passed. Accordingly, such false alarms serve as a distraction to medical personnel.

In order to minimize the distracting impact of false alarms, several techniques have been implemented. One technique includes reducing the annoyance due to lower-severity alarms, such as an alarm that results from a failed lead. That is, displays and acoustic stimuli associated with lower-severity alarms are designed in such a manner as to minimize their level of annoyance on the operator and patient by having, for instance, a proportionately lower acoustic noise level or a proportionately less distracting visual indicator. The caregiver may become unaware that there is a signal quality problem because of a "cry wolf" effect. That is, due to a series of equipment or signal related alarms, the operator may fail to investigate other alarms because of an assumption that the alarms are also related to the signal quality or equipment. A consequence of ignoring alarms is that the monitoring may become ineffective or have reduced sensitivity to serious conditions.

Another approach by which the ECG monitoring false alarm problem has been addressed is to notify medical professionals of alarms only when necessary. To implement this approach, monitoring locations have been developed where specialized personnel are responsible for the monitoring of ECG signals. That is, rather than having monitors located at bedside or at a nursing station, remote monitoring locations monitor ECG signals from multiple patients, and alarms generated by many patients are pre-screened by a human observer, sometimes called a tele-technician. When an alarm is raised, the tele-technician assesses the proper screen and decides whether to notify medical personnel such as nurses, physicians, and emergency response teams. Such an environment, however, may result in distractions that arise from multi-tasking. For example, a tele-technician may be adjusting a display to see a first patient's record in more detail, while at the same time a more critical alarm is registered by another patient. In such a situation, the critical alarm may cause the tele-technician to forget about the task of looking at the first patient's record in more detail. As such, despite the fact that a tele-technician's only responsibility may be to monitor signals, the tele-technician may still readily become overwhelmed by alarms when more than a few patients happen to have simultaneous critical alarms. Furthermore, though the alarm may sound a critical signal, it may be a false alarm, further exasperating the situation.

Communication problems can also arise due to the monitoring being done at a remote location. For example, a tele-technician may not be in close communication with a hospital ward, thus the tele-technician may have difficulty contacting hospital staff. Accordingly, due to communication issues and distraction, legitimate alarms may be missed even where alarms are monitored by dedicated tele-technicians.

Accordingly, it would be desirable to design a system capable of displaying signal quality independently of displaying waveform data, and of using the signal quality value to minimize false alarms in an ECG monitoring system.

BRIEF DESCRIPTION OF THE INVENTION

In accordance with one aspect of the invention, an electrocardiogram (ECG) monitoring system is configured to determine an index that comprises a set of indicators, where each indicator is indicative of a level of signal quality in an ECG lead. Further, the ECG monitoring system assigns a first indicator from the set of indicators to a first ECG lead signal and communicates the first indicator to a user.

In accordance with another aspect of the invention, a computer readable storage medium having stored thereon a computer program comprising instructions which when executed by a computing device cause the computing device to evaluate noise in a first electrocardiogram (ECG) lead signal, assign a first value from a quality index to the evaluated noise; and indicate the first value to a user.

In accordance with yet another aspect of the invention, a method comprises determining a condition of an ECG lead, assigning a symbol indicative of the condition of the ECG lead; and assessing the alarm from the ECG system based on the symbol.

Various other features and advantages of the invention will be made apparent from the following detailed description and the drawings.

BRIEF DESCRIPTION OF THE DRAWINGS

The drawings illustrate several embodiments presently contemplated for carrying out the invention.

In the drawings.

DETAILED DESCRIPTION OF THE PREFERRED EMBODIMENT

The invention provides a system and method for determining noise in an ECG lead signal. One or more ECG leads signals are assigned a value from an index that is indicative of the noise therein, thereby allowing an operator to assess an alarm to determine if such alarm is signal or equipment related.

Figure 1:
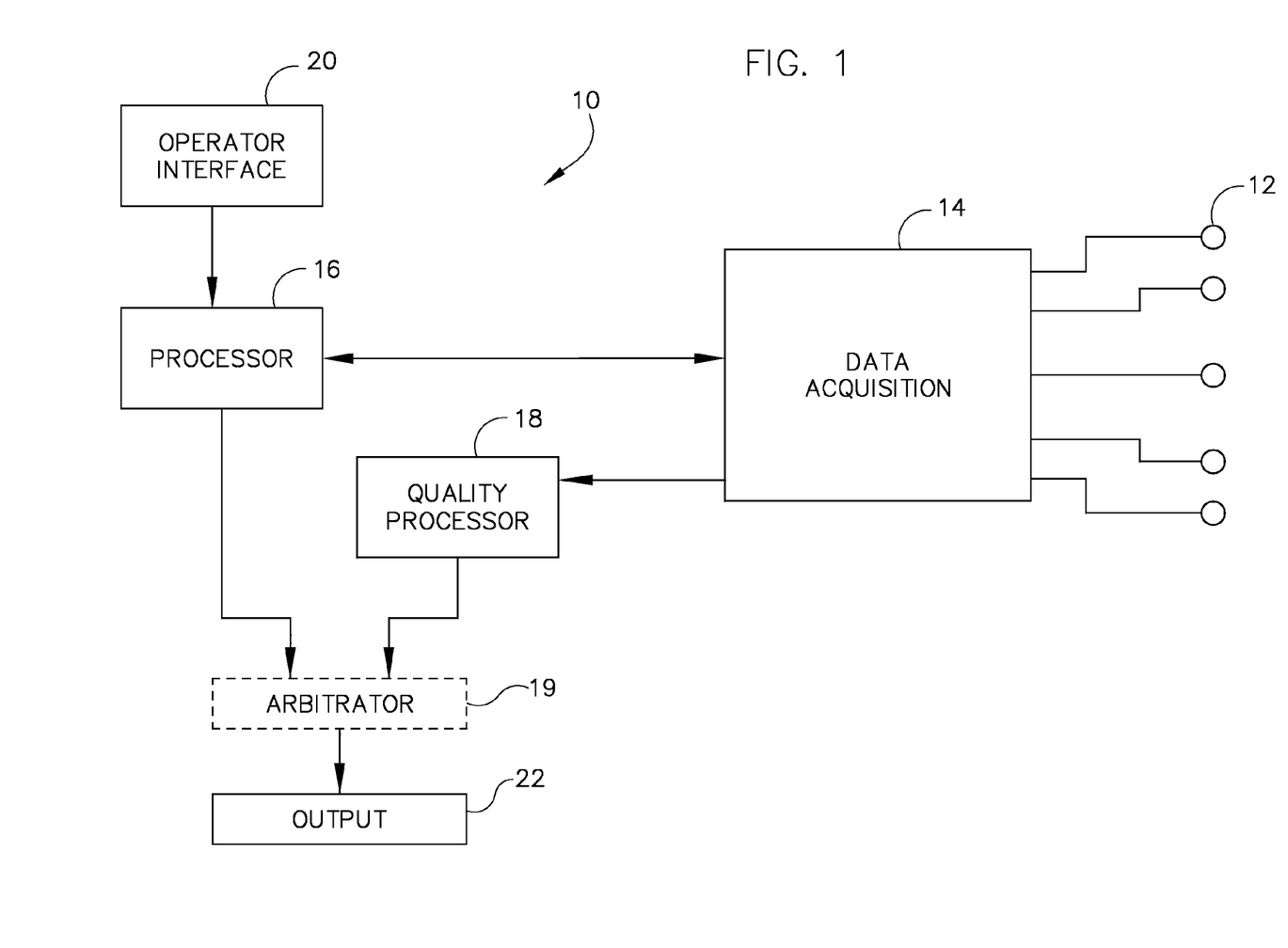
FIG. 1 is a schematic diagram of an exemplary ECG monitoring system for use with embodiment of the invention.

Referring to FIG. 1, an ECG monitoring system is depicted according to an embodiment of the invention. In the present embodiment, the ECG system 10 includes a set of electrodes 12 that are attached to the subject, a data acquisition system 14 that receives and stores ECG waveform data output from the various electrodes 12, a data processor 16 for processing the acquired ECG waveform data, and a quality processor 18 for quality analysis, which will be described more fully with respect to FIG. 2-7. In addition, it is contemplated that the ECG monitoring system 10 may also include an arbitrator 19, which will be described more fully with respect to FIG. 2. A system operator can select the operating mode of the processor via inputs to an operator interface 20. In one embodiment, the results of the ECG analyses from the processor 16 and the quality analysis from the quality processor 18 are sent to one or more output devices 22 (e.g., a display monitor, a printer, and/or a storage medium). In another embodiment, the results of the ECG analyses from the processor 16 and the quality analyses from the quality processor 18 are sent to an arbitrator 19. In such an embodiment, the arbitrator 19 may use the analysis information from the quality processor 18 to intercept or log an alarm sent from the processor 16. It is contemplated that the logged alarm may be sent to the one or more output devices 22. For example, a logged alarm may be saved into a log file of a storage medium and/or its interception may be noted in a display monitor. The quality processor 18 and arbitrator 19 of the ECG system monitoring 10 may either be manufactured into the ECG monitoring system 10 or they may be one or more add-ons of the ECG monitoring system 10.

Though the present embodiment depicts an ECG monitoring system 10 with five electrodes 12, embodiments of the invention may be used with other ECG monitoring systems that have more or less than five electrodes. Further, though the electrodes depicted are wired electrodes, it is contemplated that wireless data acquisition components may be used instead of, or in conjunction with, the wired data acquisition components.

The electrodes 12 of the ECG monitoring system 10 are attached to a subject's skin and positioned to detect electrical signals produced by the subject's heart. Applied to the electrodes is an electrically conductive gel that contacts the subject's skin and conducts electrical signals that are present at the skin to the electrode. The subject's heart produces an electrical signal that is referred to as an ECG waveform. The standard nomenclature identifies a P wave, a QRS complex, a T wave, and a U wave.

An ECG waveform for a single beat is typically referred to as a PQRST complex. The P wave appears at initiation of the beat and corresponds to activity in the atria, while the QRST complex follows the P wave and corresponds to ventricular activity. The QRS component represents the electrical activation of the ventricles, while the T wave represents the electrical recovery thereof. The ST segment is a relatively quiescent period. One or more of these waves may be distorted or even absent in patients with various forms of heart disease or disorder. Often patients exhibit occasional distorted beats, termed pre-ventricular contractions (PVC's) containing very large R waves. These physiologically-generated heart waveforms should not be mistaken for signal quality variations.

Information gathered from the data acquisition component 14 of the ECG monitoring system 10 is used to generate ECG lead signals. For example, in one embodiment, the data acquisition component 14 may determine four ECG lead signals from the five electrodes 12. That is, potential difference between pairs of electrodes (or linear combinations of these differences) 12 may be used to generate a unique ECG lead signal, which may be displayed or indicated at the output 22. That is, one or more ECG lead signals are often derived from data acquired from two or more electrodes. Such ECG lead signals or often called derived leads. As such, with regard to derived leads, often there is not only one unique electrode associated with each ECG lead signal. Accordingly, there may be more ECG lead signals than electrodes. Embodiments of the invention may be used with ECG systems that employ derived leads.

Figure 2:
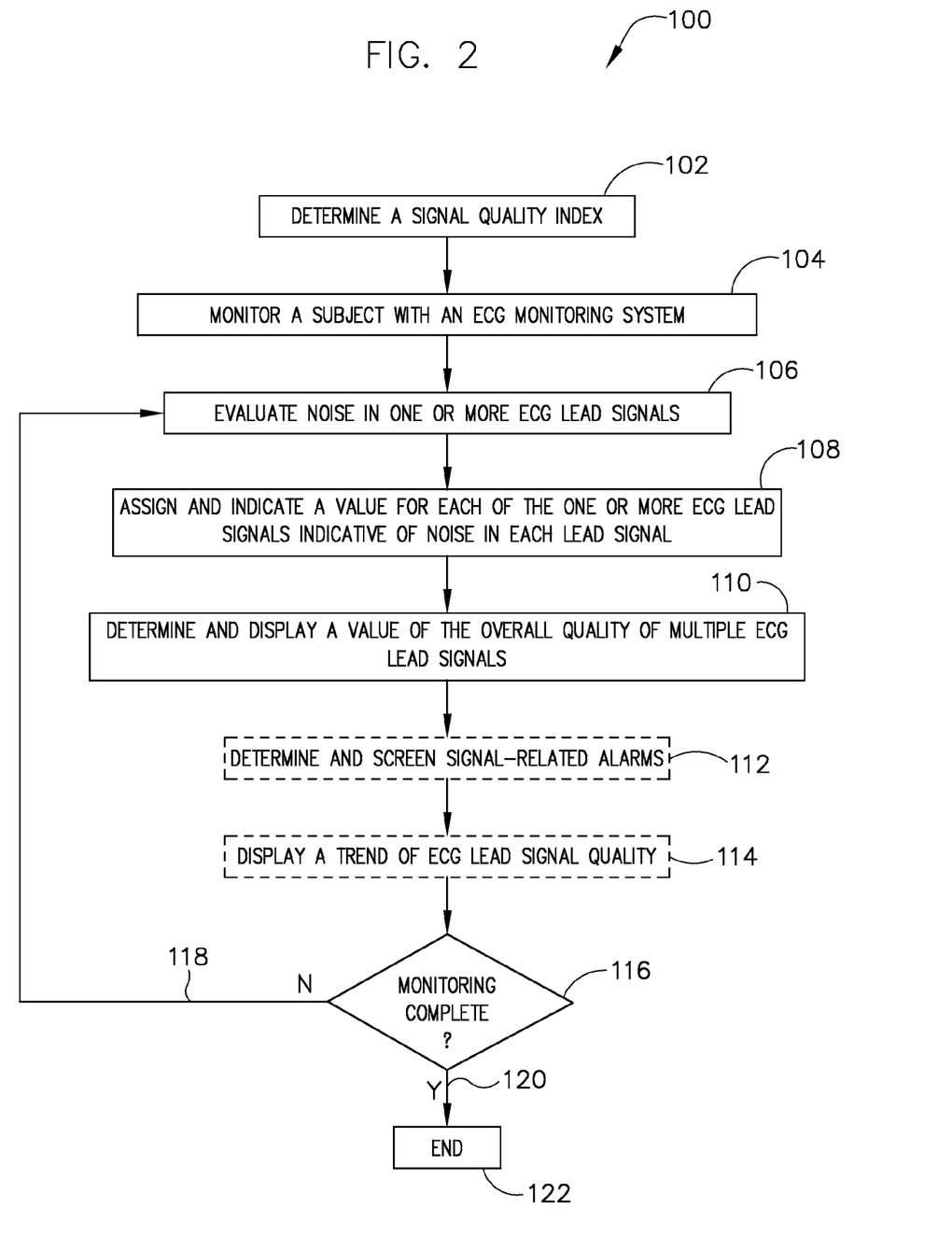
FIG. 2 is a flowchart depicting a technique according to an embodiment of the invention.

Referring to FIG. 2, a flowchart depicts an ECG signal quality indication technique 100 according to an embodiment of the invention. Technique 100 provides for the determination and display of a signal quality of one or more leads associated with ECG monitoring systems. Further, technique 100 provides for the determination and display of an overall signal quality index of multiple leads associated with an ECG monitoring system. In addition, a trend of each quality (i.e., signal quality of one or more leads and overall signal quality) may be determined and displayed to an operator. Such a trend allows indication or display of signal quality over time such that electrode failure may be anticipated so that an electrode may be re-applied or replaced before failure occurs. Such indicators (i.e., signal quality, overall quality of multiple leads, or trends) can be used to evaluate alarms initiated by the ECG monitoring system. That is, when an alarm in an ECG system activates, the signal quality associated with the one or multiple ECG lead signals, or trends obtained therefrom, may be used to determine whether the alarm is a signal quality or equipment related alarm that does not necessitate immediate action. On the other hand, the signal quality associated with the one or multiple ECG lead signals, or trends obtained therefrom, may be used to determine that an alarm is not signal quality related, thus requiring immediate attention.

Technique 100 begins with the determination of a signal quality index at STEP 102. The index comprises a set of indicators or symbols which are indicative of signal quality or condition of one or more ECG lead signals. In other words, the indicators are indicative of the type and/or magnitude of noise in an ECG lead signal. The quality may be displayed as a set of numerical indicators, a set of colors, or audible signals, and the like. For example, in one embodiment, the index may include a set of consecutive real numbers ranging from zero to one. In such an embodiment, zero may indicate low quality, one may indicate high quality, and the real numbers therebetween indicate increments of the quality. In another embodiment, values of the index are colors. For example, colors ranging from red to green could be used, where red indicates a low signal quality and green indicates a high signal quality. In yet another embodiment, the quality index includes a range of audible tones or sounds where a low-noise tone, or low frequency tone, indicates low quality and high noise or high tone indicates a high quality. After a signal quality index is determined, a subject is monitored by an ECG monitoring system, such as the ECG monitoring system 10 of FIG. 1, at STEP 104.

As shown, FIG. 2 depicts a signal quality index (i.e., an "index") that is determined at STEP 102 before a subject is monitored by an ECG system. For example, the index could be a factory setting hard-set into the ECG monitoring system (e.g., 10 of FIG. 1). However, it is also contemplated that the index could be determined after monitoring of a subject begins at STEP 104. Thus, despite the order in which the signal quality index is determined, the quality of one or more ECG lead signals is evaluated or determined at STEP 106. In other words, at STEP 106, the magnitude and/or type of noise in one or more ECG lead signals is evaluated or determined. The manner in which an ECG lead signal is evaluated and its quality determined will be further discussed below with respect to FIGS. 3-7.

As mentioned, still referring to FIG. 2, noise in the one or more ECG lead signals is evaluated at STEP 106, and, upon determining or evaluating the quality thereof, an indicator or value indicative of ECG lead signal quality is assigned to each of the one or more lead signals, and each value is also indicated to a user at STEP 108. Such value may be indicated or displayed via a computer screen (e.g., see output 22 of FIG. 1). In one embodiment where, for instance, five leads are evaluated, five values, each indicative of a signal quality, may be stored in computer memory and later or immediately indicated to a user in one or more of the manners described above. Accordingly, if the ECG monitoring system (e.g., monitoring system 10 of FIG. 1) presents an alarm, the user may evaluate the alarm in light of the indicated or communicated signal quality associated therewith. For example, if the value assigned to the third lead signal indicates that the signal quality is low, the user may determine that an alarm associated therewith is likely a signal or equipment-related alarm and thereby determine that the alarm is false. Alternatively, if the value indicates that the signal quality of the third lead is high, the user may determine that the third lead alarm is not an alarm related to signal quality and that action is needed. Furthermore, multiple alarms associated with multiple leads may be likewise assessed, where each ECG lead signal is associated with a respective quality indicator. Thus, one or more alarms associated with low quality indices may thereby be determined to be false or related to signal quality. On the other hand, one or more alarms associated with high quality indices may thereby be determined to be not false, thus necessitating action.

It is again noted that an ECG lead signal may be associated with more than one electrode. By assessing multiple lead indicators, an operator may be able to determine that an electrode is failing or that one or more ECG lead signals are poor. To illustrate, take two ECG lead signals, I and II, that are each associated with poor signal indices. Further, for purposes of illustration, take ECG lead signal I and II as being derivative leads, where signal I is associated with electrode A and B and lead signal II is associated with electrode A and C. If the lead signal indicators for each lead are poor, an operator may determine that the indices are poor because electrode A is failing. That is, it may be determined that electrode A is failing or its signal is poor because electrode A is common to each ECG lead signal. An electrode may fail for a variety of reasons. For example, the electrode itself may be malfunctioning, or the electrode may be failing because there is poor electrode-patient contact or placement.

At STEP 110, a value indicative of overall quality in multiple leads may be also assigned and indicated to the user. That is, it is contemplated that a single signal quality indicator or value may be assigned to multiple leads, indicating their combined overall signal quality. This overall signal quality indicator would be determined from, in part, the individual signal qualities associated with the ECG leads that are associated with the overall signal quality. In one embodiment, one value that indicates the overall signal quality of each ECG lead associated with an ECG monitoring system may be displayed to a user. Accordingly, instead of viewing the signal quality of each indicator associated with a subject, an operator may simply view the combined overall quality of several or all ECG leads associated with the subject. If the overall signal quality is high, an operator may determine that any active alarm associated with the ECG monitoring system is not signal related and is, therefore, not a false alarm. On the other hand, if the overall signal quality is low and an alarm is active, an operator may determine from the overall poor signal quality that the alarm is likely signal related, is false, and does not require immediate attention. Further, an operator may then further investigate the signal quality of individual ECG leads to determine which of the one or more ECG leads is causing the overall signal quality to be poor. Though it may be preferable to determine and indicate an overall signal quality of all leads associated with a subject, it is contemplated that an overall signal quality of less than all ECG lead signals could be determined and indicated.

The manner in which the overall signal quality is determined will be affected by the number and type of leads that will be associated with the overall signal quality. To illustrate, take for example, the determination of an overall quality of four lead signals: lead signal I, lead signal II, lead signal V1, and lead signal V2. Further, take an overall signal quality index that ranges from zero to one, where zero represents a poor signal quality and one represents a good signal quality. To determine an overall quality of the four listed lead signals, the individual lead signal qualities may be weighted and then summed. For example, if lead signals V1 and V2 are derived signals (i.e., derivative leads), they may be assigned weights that are less than the non-derived lead signals (e.g., lead signals I and II in this example). As such, lead signals I and II may each be weighted by multiplying their respective signal quality values by, for instance, 0.4. Lead signals V1 and V2, on the other hand, may be weighted by multiplying each of their respective signal quality values by, correspondingly, 0.1. Accordingly, in this example, the overall lead signal value of lead signals I, II, V1, and V2 is thereby the sum of their respective weighted signal quality values.

In one embodiment, it is contemplated that process control proceeds to STEP 112 (shown in phantom) to determine and screen signal-related or false alarms. At STEP 112, an arbitrator (e.g., arbitrator 19 of FIG. 1) may automatically determine that an alarm generated by an ECG monitoring system such as system 10 shown in FIG. 1 is a signal-related alarm and, as such, may screen the signal-related alarm. That is, if an alarm is associated with one or more ECG lead signals having a poor signal quality index or indicator, the arbitrator may determine that the alarm is signal-related or false and screen the alarm in a variety of ways. For example, the arbitrator may screen the alarm at STEP 112 of FIG. 2 by logging the determined signal-related alarm into a log file without sounding an acoustic warning signal. In another example, the arbitrator may screen the alarm by intercepting such alarm before it is displayed to a user. As such, signal-related alarm will not be communicated to a user. Accordingly, the user will not need to determine whether or not the alarm is signal-related or not. In such an example, the interception of the signal-related alarm may be also noted in a log file and/or the user could be notified via a display that an alarm has been intercepted. The qualifications of what may be a poor index or indicator such that a signal-related alarm may be determined and screened at STEP 112 may be factory set into the ECG monitoring system or the add-on components thereof, or a user may manually determine and pre-configure what range of values qualify as a poor index or indicator.

It is also contemplated, as shown in phantom at STEP 114, that a trend indicative of signal quality over time of one more leads may be determined and indicated. For example, according to an embodiment, if signal quality of an ECG lead has been evaluated more than once over time, a trend may be present that indicates lead signal quality over time. Likewise, a trend may be present that indicates the overall signal quality of multiple leads over time. That is, a trend may indicate to a user that the signal quality (or an overall signal quality) has been decreasing over time, remaining steady over time, or increasing over time. Such indications may be of value to a user in assessing whether alarms associated therewith are signal related or not, or to anticipate a forthcoming electrode failure. For example, if a trend indicates that signal quality is decreasing over time, a user may determine that a particular lead will likely fail in the future. As such, a trend can alert a user that an electrode associated with an ECG lead signal may need to be replaced or re-applied. As such, in one embodiment, a trend may be used to anticipate or predict a lead failure event.

In another embodiment, a trend is displayed that is indicative of signal quality over time of multiple leads. For example, if one overall value was assigned to five leads and the five leads have been re-evaluated, resulting in another five lead overall signal quality value being assigned and displayed, a trend of such values may be determined and indicated at STEP 114. Of course, it is contemplated that more than two signal values may be used to determine a trend of signal quality over time such as a set of values determined from an evaluation and following re-evaluations. The trend in the previously-mentioned example would be indicative of the overall signal quality, over time, of the five leads. Accordingly, if a user determines from the trend that the overall quality of the five leads is diminishing, a user may deduce that the quality of one or more of the leads is diminishing, causing the overall quality to diminish, thus enabling the user to anticipate that subsequent alarms may be inaccurate. As such, because a display of each lead signal may not typically be found on a primary viewing screen, a user can scan through viewing screens to determine which of the one or more leads suffers from a low signal quality. Again, it is contemplated that more than two signal values may be used to determine a trend of signal quality over time.

Whether or not a trend is determined, process control proceeds to decision STEP 116 where it is determined whether or not monitoring is complete. If monitoring is not terminated 118, process control proceeds back to STEP 106, after which signal quality in the one or more leads is evaluated or re-evaluated. On the other hand, process control proceeds to an end at 122 if it determined that monitoring is complete 120. Accordingly, technique 100 allows for individual or multiple ECG lead signals to be monitored by having signal qualities and trends associated therewith determined and indicated. As such, technique 100 enables a user to assess ECG lead signal quality and determine whether alarms are noise related or not, thus whether they are false alarms or not.

Figure 3:
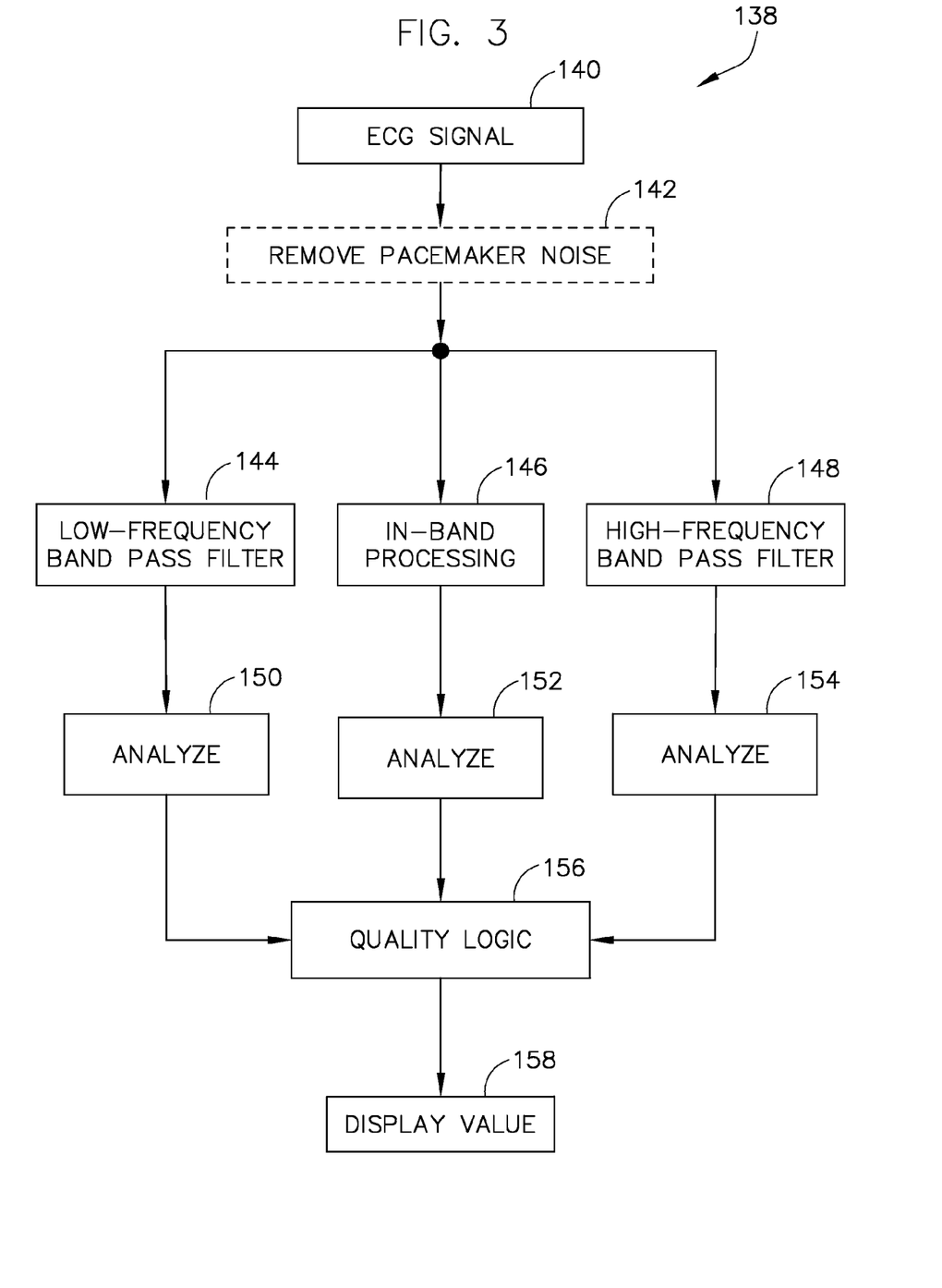
FIG. 3 is a graphical representation of an embodiment illustrating ECG lead signal indexing and display.

Quality in an ECG lead signal may be determined and displayed according to technique 138, as illustrated in FIG. 3, and as performed in STEPs 106 and 108 of FIG. 2. According to the embodiment shown in technique 138, process control begins with an ECG lead signal 140. In the illustrated embodiment, the ECG lead signal 140 is a signal determined from two or more electrodes, such as one or more of the electrodes 12 shown in FIG. 1. In one embodiment, pacemaker beats that may be present in an ECG lead signal 140 are removed at STEP 142 (shown in phantom). That is, if the subject being monitored has a pacemaker, signals associated therewith may be removed at STEP 142 to aid in the assessment of signal quality that will be described below. An embodiment depicting pacemaker beat removal will be further described with respect to FIG. 7.

Whether or not pacemaker noise is removed from the ECG lead signal 140, at STEP 142, the ECG lead signal 140 or representation thereof passes into three preparation components 144, 146, 148 such that the signal may be prepared for analysis or evaluation. One preparation component is a low-frequency band pass filter 144. In one example, a low-frequency band pass filter such as a Chebyshev Type I filter with an order of n=1 is used. Such a low-frequency band pass filter 144 may have low and high cut-off frequencies of 0.1 and 0.7 HZ, respectively, and a peak-to-peak ripple in the passband of 0.5 dB. Such cut-off frequencies may allow the DC component of the ECG wave and the "P" and "T" waves, associated with cardiac QRS complexes as known in the art, to be filtered out. As such, noise within the ECG lead signal 140 that is within the frequency range passed by the filter will remain therein. In other words, noise within a specified frequency range is captured or extracted as the output from the low-frequency band pass filter 144.

A second preparation component 146 includes in-band processing logic. As with the low-frequency band pass filter 144, the ECG lead signal 140 or representation thereof is passed through the in-band processing 146. As a result of passing the ECG lead signal 140 through the in-band processing 146, noise is captured or extracted in the in-band processing 146 output. Further details regarding the in-band processing 146 will be more fully described, below, with respect to FIGS. 4-6.

A third preparation component 148 includes a high-pass filter 148. For example, in one embodiment a high-pass filter such as a Chebyshev Type I filter with an order of n=4 having cut-off frequencies of 40 HZ and having peak-to-peak ripple in the passband of 0.5 dB is employed. The filter, by having an order of n=4, allows for fast roll-off in the stop-band. As with the other components 144, 146, the ECG lead signal 140 or representation thereof is allowed to pass through the third component 148. Because non-pacemaker QRS complexes generally do not have frequencies above 40 Hz, noise disturbances are captured or extracted from the output in of the third component 148.

It is contemplated that other preparation components may be used in a manner consistent with the invention. The preparation components used in the present embodiment were chosen such that particular noise components may be extracted from an ECG lead signal. As will be described below, these noise components will be analyzed. Based on an a priori data set, it was determined that the analysis of the particular noise components may be used to effectively determine the signal quality of an ECG lead signal. However, it is contemplated that other outcomes could be determined from the same or different data set set(s). That is, it may be determined that preparation components having different parameters than those listed could be used in a manner consistent with the invention.

The outputs from each of the three preparation components 144-148 are individually analyzed in respective analysis steps 150-154 to determine their contribution to the signal quality.

For example, in one embodiment, output from the first preparation component 144 is allowed to pass through a first analysis at STEP 150, which employs an exponential threshold function nonlinearity that maps the signal to real numbers between zero and one. The real number, ranging from zero to one, indicates a signal quality of the portion of the ECG Lead signal that is associated with the analysis at STEP 150. In one embodiment, the following exponential function, having a soft threshold, may be employed:

$$v_{1,i}[n] = \begin{cases} 1 - \frac{1}{\exp(50-1)}(\exp(50|y_{1,i}[n]|) - 1), & \text{if } |y_{1,i}[n]| < \text{threshold,} \\ 0 & \text{otherwise.} \end{cases} \quad \text{(Eqn. 1)}$$

With regard to this first analysis at STEP 150, a threshold of 0.3 mV may be employed. In the present embodiment, threshold violations within 200 msec will be added or combined. By combining such violations, persistent effects of a condition may be captured. For example, a periodic artifact caused by, for instance, the patient brushing teeth may cause several violations in an ECG signal over a short time period. Thus, by combining violations that occur within 200 msec of one another, the signal quality over the course of teeth brushing may be degraded. Because this exponential function, Eqn. 1, has a soft threshold, a value from zero to one may be mapped onto the component of the signal being analyzed. For example, a very noisy signal may have a zero mapped onto it, whereas a clean signal may have a one mapped onto it. Because a soft threshold is implemented, values between zero and one may also be mapped onto the signal.

In a similar manner, output from the second preparation component 146 is allowed to pass through a second analysis at STEP 152, which also may employ an exponential threshold function having a soft threshold, where the function maps the signal to real numbers from zero to one. Again, the real number, zero, one, or an increment therebetween, indicates the signal quality of the portion of the ECG Lead signal that is associated with the analysis step 152 of the in-band processing component 146. In one embodiment, the following exponential function may be employed:

$$v_{2,i}[n] = \begin{cases} 1 - \frac{1}{\exp(50-1)}(\exp(50|y_{2,i}[n]|) - 1), & \text{if } |y_{2,i}[n]| < \text{threshold,} \\ 0 & \text{otherwise.} \end{cases} \quad \text{(Eqn. 2)}$$

With regard to the second analysis at STEP 152, a threshold of 0.2 mV may be employed. In the present embodiment, threshold violations within 200 msec of one another may be added or combined to reflect persistency of condition effects.

With regard to the output from the third preparation component 148, it is allowed to pass through a third analysis at STEP 154, which employs another exponential threshold function that maps the signal to real numbers from zero to one. The real number, greater than or equal to zero and less than or equal to one, represents the quality of the portion of the ECG lead signal that is associated with the third analysis at STEP 154. In one embodiment, the following exponential function may be employed:

$$v_{3,i}[n] = \begin{cases} 1 - \frac{1}{\exp(50-1)}(\exp(50|y_{3,i}[n]|) - 1), & \text{if } |y_{3,i}[n]| < \text{threshold,} \\ 0 & \text{otherwise.} \end{cases} \quad \text{(Eqn. 3)}$$

With regard to the third analysis at STEP 154, a threshold of 0.025 mV may be employed. Again, in the present embodiment, threshold violations within 200 msec of one another will be added or combined to reflect persistency of condition effects.

As presented, the noise captured or allowed to pass through the three preparation components 144-148 are each passed through respective analyses at STEPs 150-154. The exponential functions employed during the analyses at STEPs 150-154 in the present embodiment are exemplary. The functions were chosen to correspond with findings that were obtained from analyzing an a priori data set that included waveform information from a large set of individuals. However, it is contemplated that other functions could be employed in a manner consistent with the invention. That is, the functions may be tailored to suit preferred outcomes. As an example, hard thresholds could be employed rather than soft thresholds. In such an instance, for example, an analyzed signal would only have a zero or one mapped onto it. That is, there would be no values between zero and one that would be mapped onto the analyzed signal. As such, a value of zero, for example, would indicate that the ECG lead signal is poor, and a value of one may indicate that the ECG lead signal is clean, or at least relatively clean.

Not only is it contemplated that other exponential functions may be employed, it is contemplated that other, or different, components of ECG lead signal noise may be prepared and analyzed. For example, instead of employing three components 144-148 to prepare ECG lead signal noise, less than or more than three preparation components could be employed. As such, less than three or more than three frequency bands of ECG lead signal noise may be prepared and analyzed to determine the quality of the ECG lead signal.

Upon passing the outputs from the preparation elements or components 144-148 through the respective analyses at STEPs 150-154, output signals from the analyses at STEPs 150-154 are passed through quality logic at STEP 156. In one embodiment, the quality logic equally combines the outputs from the analyses at STEPs 150-154. That is, each of the outputs of the three analyses at STEPs 150-154 may be multiplied by one-third and then summed. As such, the signal quality of low, in-band, and high-frequency noise components of an ECG lead signal 140 are combined so that a single indicator may be assigned to the ECG lead signal 140. In another embodiment, each the outputs from the three analyses at STEPs 150-154 could be first summed, and then the sum may be multiplied by one-third. Outputs from the quality logic at STEP 156 are then passed through a moving average filter (not shown) of, for example, six seconds, and an index value is determined and indicated or displayed at STEP 158. As such, the value is an indicator of the quality of the ECG lead signal 140. As discussed, in the present embodiment the output from the analyses at STEPs 152-156 are equally combined. However, it is contemplated that, in an alternate embodiment, the outputs of the analysis steps may not be combined equally. For example, it may be determined that the low frequency noise has less of an impact on signal quality than each of the in-band and high frequency components. As such, the output from the analysis of the low-frequency noise may be weighted less than the output from each of the in-band and high-frequency noise analysis.

Figure 4:
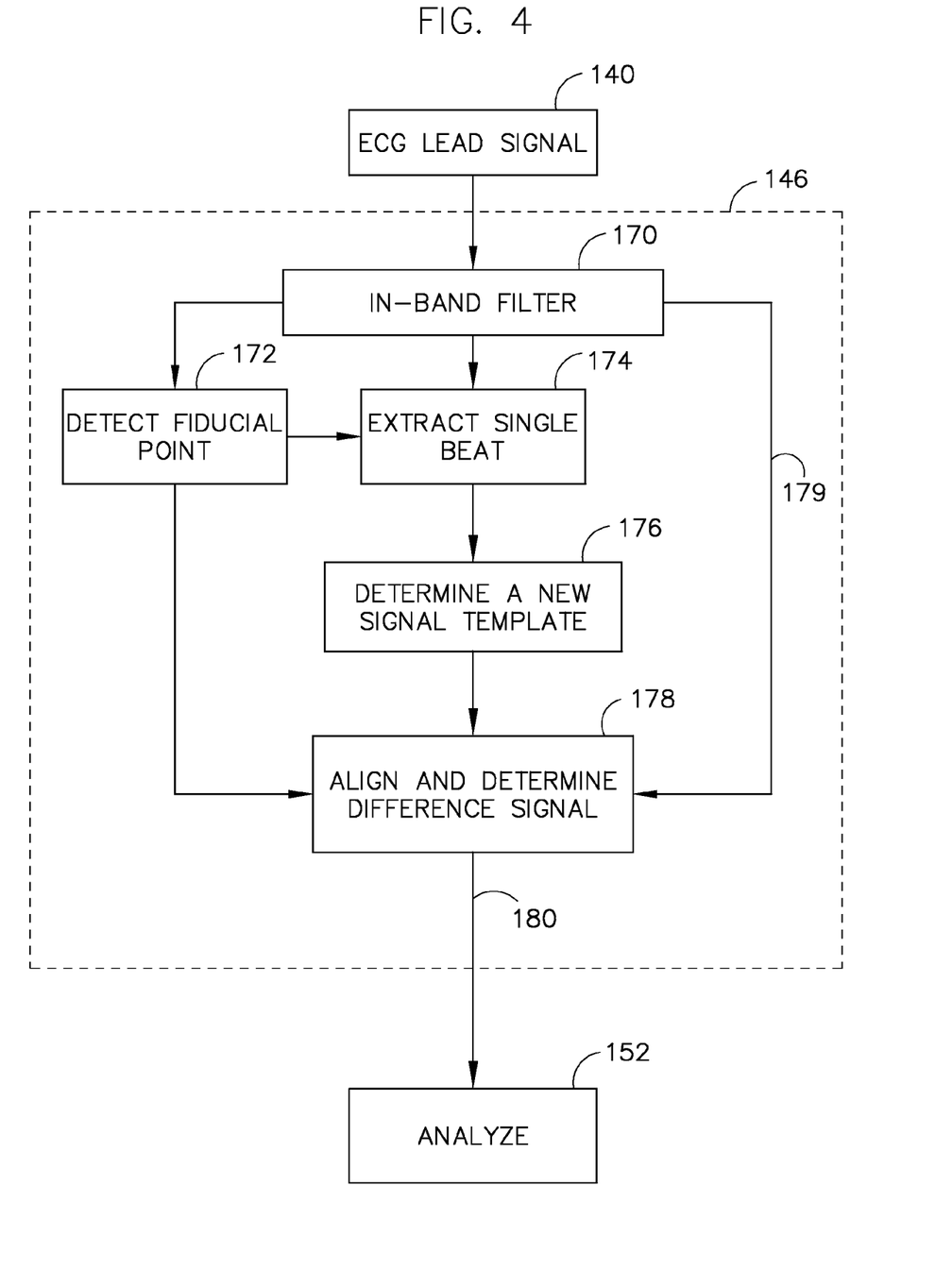
FIG. 4 is a graphical representation of an embodiment depicting the in-band processing of FIG. 3.

Referring now to FIG. 4, a graphical depiction of the in-band processing at STEP 146 of FIG. 3 is shown. As shown, the ECG lead signal 140 is allowed to pass through an in-band filter at STEP 170 of the in-band processing component and its accompanying logic of 146. The in-band filter at STEP 170 may have, for example, cut-off frequencies of 0.7 Hz and 40 Hz. That is, frequencies from 0.7 Hz to 40 Hz will be allowed to pass through the in-band filter at STEP 170. Fiducial points present in the output of the in-band filter at STEP 170 are then detected at STEP 172. The fiducial points represent points in time where the ECG lead signal has a maximum of energy. As such, there is a single fiducial point or time point corresponding to each heart beat represented in the ECG lead signal 140. Accordingly, and as will be further described below, the detected fiducial points 140 may be used to align signals and/or identify heart beats.

Though in FIG. 4 it is shown that the fiducial points are detected after the ECG lead signal 140 is passed through the in-band filter at STEP 170, it is contemplated that the fiducial points could be detected before the ECG lead signal 140 is allowed to pass through the in-band filter at STEP 170. A manner in which fiducial points may be detected will be set forth with respect to FIG. 6.

Still referring to FIG. 4, using the detected fiducial points from STEP 172, a single beat is extracted at STEP 174 from the output of the in-band filter at STEP 170. That is, the time points (i.e., the detected fiducial points from STEP 172) are used to identify and extract a single beat at STEP 174. A new signal template or QRS complex template is then determined at STEP 176.

A beat template is a representation of a recent beat that, by design, does not contain artifact-causing noise. A signal template, on the other hand, is a representation of a series of beats that, in theory, do not contain artifact-causing noise. The manner in which the new signal template is determined at STEP 176 will be more fully described with respect to FIG. 5. At STEP 178, the new signal template determined at STEP 176 and the output 179 of the in-band filter at STEP 170 are aligned using the fiducial points detected at STEP 172. Further, once aligned, the difference between the determined signal template of STEP 176 and the series of beats present in the in-band filter output 179 is also determined at STEP 178. Accordingly, because the new signal template determined at STEP 176 preferably contains beat information without noise and the output 179 from the in-band filter contains beat information that may contain noise, the difference determined at STEP 178 results in an output 180 that only contains noise representative of any noise that may have be present in the output 179 of the in-band filter at STEP 170. Though it is preferable that the output 180 contains only noise information, it is contemplated that in practice, a small amount of beat information may remain in the output 180. Once the difference signal is determined at STEP 178, the output 180 is analyzed at STEP 152 as described above with respect to FIG. 3.

Figure 5:
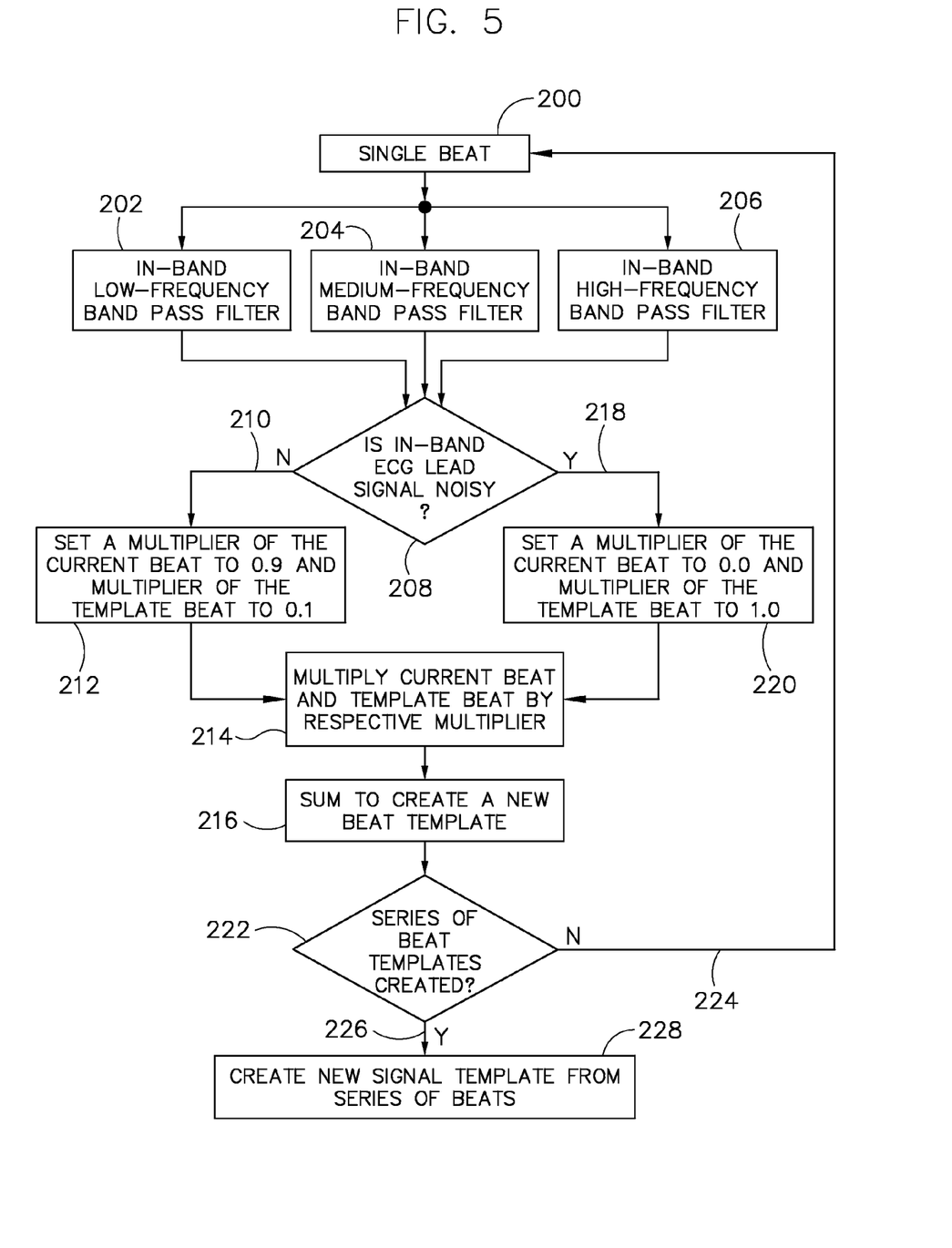
FIG. 5 is a flowchart depicting an embodiment of the determination of a new signal template shown in FIG. 4.

Referring to FIG. 5, a graphical representation of the logic used to determine the new signal template 176 of FIG. 4 is shown according to an embodiment. A single beat 200, which was extracted (see STEP 174 of FIG. 4) using the output of the in-band filter (see 170 of FIG. 4) and the detected fiducial points (see STEP 172 of FIG. 4), is allowed to pass in parallel through three filters at STEPs 202-206: a low-frequency band pass filter at STEP 202, a medium-frequency band pass filter at STEP 204, and a high-frequency band pass filter at STEP 206. In one embodiment, each of the filters at STEPs 202-206 are a Chebyshev Type I filter of order n=4 and have a peak-to-peak ripple of 0.5 db. The low-frequency band pass filter at STEP 202 may have cut-offs of 0.7 Hz and 5 Hz. The medium-frequency band pass filter at STEP 204 may have cut-offs of 5 Hz and 25 Hz. Next, the high-frequency band pass filter at STEP 206 may have cut-offs of 25 Hz and 40 Hz. At decision STEP 208, the outputs of these filters at STEPs 202-206 are used to determine whether the single beat 200 is noisy. The truth table shown below illustrates the logic that may be used to determine whether or not the beat is noisy at decision STEP 208.

TABLE 1

NOISE DETERMINATION LOGIC

| In-band Low Frequency Violations? | | In-band Medium-Frequency Violations? | In-band High-Frequency Violations? | |
|---|---|---|---|---|
| Mean | Standard Deviation | Standard Deviation | Standard Deviation | Is Beat Noisy? |
| Y | Y | N | X | Y |
| Y | Y | Y | X | N (PVC, VEB) |
| Y | N | N | X | Y |
| Y | N | Y | X | N (PVC, VEB) |
| N | Y | N | X | Y |
| N | Y | Y | X | N (PVC, VEB) |
| N | N | X | X | N |
| X | X | X | Y | Y |

In Table 1, the term "Y" represents that a statistical amplitude violation has occurred with respect to the appropriate frequency component. For example, "Y" may represent that the mean and standard deviation of the respective frequency component violated the appropriate threshold. The term "N" of Table 1 represents that a statistical amplitude violation has not occurred with respect to the appropriate frequency component. The term "X" represents that it is not relevant that a frequency violation has or has not occurred with respect to the appropriate frequency component (i.e., a "don't care"). For example, as shown in Table 1, if an in-band high frequency violation "Y" occurs, the beat is determined to be not noisy whether or not amplitude violations occurred in the low and medium frequencies. The acronyms PVC and VEB associated with the "beat is not noisy" determination indicate that the over-limit conditions associated therewith were likely due to premature ventricular contractions (PVC) and/or ventricular ectopic beats (VEB). PVCs and VEBs are normal beat variants, and are not associated with poor signal quality. In addition, it is noted, that in one embodiment, also represented in Table 1, if there is no high-frequency violation but there is a medium frequency violation, the beat is considered not noisy whether or not there was a low-frequency violation. In such an instance, it is assumed that a medium frequency violation is a result of a subject having an irregular or distorted heartbeat, such as a PVC or VEB, rather than the subject's heartbeat containing enough noise to trip a violation. As such, it is assumed that such a beat is not noisy whether or not there was a low-frequency violation.

In one embodiment, a high-frequency violation occurs when the standard deviation of the output from the high-frequency band pass filter at STEP 206, computed over the present beat interval, exceeds 0.1 mV. The thresholds corresponding to the low and medium frequency violations, on the other hand, may be set to one hundred and fifty percent of the average mean and standard deviation over the previous five beats outputted from the appropriate filter at STEPs 202, 204.

That is, the five beats preceding the current beat 200. As depicted in the logic of Table 1, normal physiological variant heartbeats, such as PVCs and VEBs from both normal and medically abnormal subjects, are treated as normal beats. Since these physiological variant heartbeats are not due to artifactual sources, they will be removed, or at least substantially removed, during STEP 178 of FIG. 4 such that they are absent or substantially absent in the difference signal output 180. The logic of Table 1 is effective from one subject to the next and is effective for a single subject with normal long-term ECG amplitude variations (e.g., diurnal variations) in heartbeat amplitude because the logic adapts the criteria for beat detection to underlying waveform properties and to normal beat-to-beat and patient-to-patient amplitude variations of recent heartbeats. As such, system re-configuration from one patient to the next is not needed.

The new beat template that will be created at STEP 216 of FIG. 5 will be used to determine the difference signal (i.e., output 180 shown in FIG. 4). For example, in one embodiment, the initial beat template is the average of ten non-noisy subject beats. As additional beats pass through the in-band processing component at STEP 146 (shown in FIG. 3) a new beat template used for determining the difference signal 180 may be created or determined. For example, if the beat 200 is determined to be not noisy 210 at decision STEP 208, a multiplier of the current beat 200 is set to 0.9 and the multiplier of the beat template is set to 0.1 at STEP 212. The current beat 200 and the beat template is then multiplied by its respective multiplier at STEP 214. Accordingly, a new beat template is formed at STEP 216 by summing the product of current beat 200 and its multiplier (e.g., 0.9) and the product of the beat template and its multiplier (e.g., 0.1).

On the other hand, if the beat 200 is determined to be noisy 218 at decision STEP 208, a multiplier of the current beat 200 is set to 0.0 and the multiplier of the beat template is set to 1.0 at STEP 220. At STEP 214, the current beat 200 and the beat template is then multiplied by its respective multiplier. In other words, the new beat template created at STEP 216 consists of the previous beat template, since the current beat was found to be too noisy to be used in the creation of a new beat template. Since a beat template is formed using subject's own ECG waveform, the beat template is less sensitive to the variations in the ECG waveform over the population, but it may be more sensitive to the variations within the subject's own waveform. Thus, by increasing the weight on the current beat, the sensitivity to the beat-to-beat variations may be minimized. Accordingly, technique 176 allows for subject-to-subject variances to be accounted for.

After creating the new beat template at STEP 216, process control proceeds to decision STEP 222. At decision STEP 222, it is determined whether or not to repeat beat template creation for another beat. In one embodiment, the new signal template that is input to determine the difference signal at STEP 178 of FIG. 4 comprises a series of beats. As such, the difference signal that is output 180 comprises noise over a series of beats. Accordingly, if a series of new beat templates has not been created 224, process control repeats the creation of other new beat templates at STEPs 200-216. This repetition continues until the series of beats templates is determined. The amount of beats that are needed in order to have a series of beat templates may be set by an operator or factory set into the ECG equipment. To continue, if it is determined at decision STEP 222 that the series of beat templates has been determined 226, process control proceeds to STEP 228, where the series of new beat templates are strung together to create or determine the new signal template at STEP 176. As previously discussed, such signal template created at STEP 228 is used to create the difference signal output 180, found in FIG. 4. In turn, the output 180 is analyzed at STEP 152, as shown in FIGS. 3 and 4.

Figure 6:
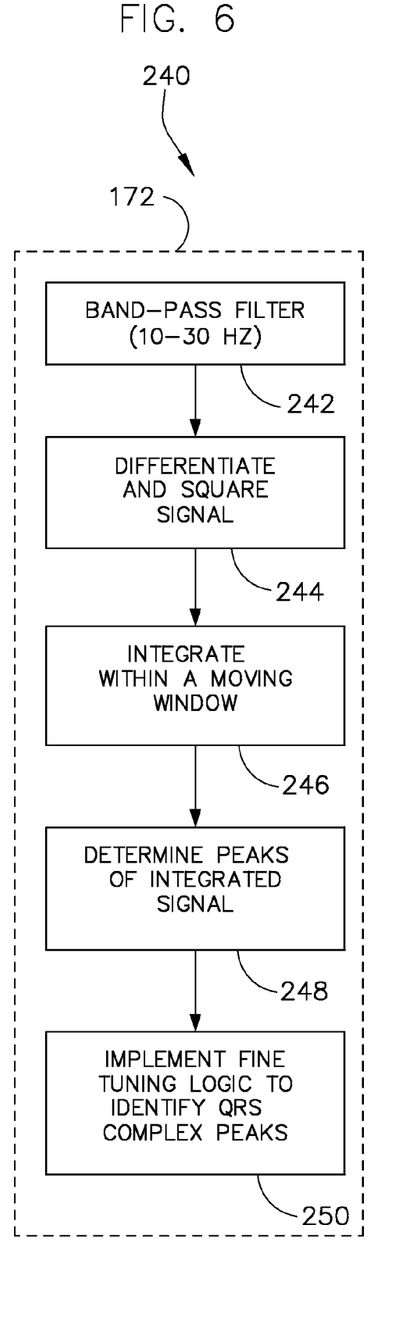
FIG. 6 is a flowchart depicting an embodiment of the detection of fiducial points shown in FIG. 4.

As discussed with respect to FIG. 4, the logic of the in-band processing includes the detection of fiducial points (see STEP 172 of FIG. 4). In FIG. 6 a technique is depicted for detecting fiducial points at STEP 172 according to an embodiment. Technique 240 with the output of the in-band filter at STEP 170 (shown in FIG. 4) being passed through a band pass filter at STEP 242 having cut-offs of 10 HZ and 30 Hz. In one example, a Chebyshev Type I filter of order 4 and peak-to-peak ripple of 0.5 dB in the pass-band is used. At STEP 244 the output from the filter at STEP 242 is differentiated and squared. The first order differentiation amplifies the changes from the baseline and squaring emphasizes the high frequency components (i.e., peaks). The differentiated and squared output is integrated within a moving window having a length of, for example, 50 msec at STEP 246. STEP 246 provides a measure of energy distribution of the signal within a short period of time. As such, STEP 248 outputs the peaks of the integrated signal as time points. These peak points are, as they are known by those in the art, potential QRS complexes. However, some subjects have T-waves with high amplitudes that mask the QRS complex or result in incorrectly identifying T-waves as QRS complexes. Therefore, at STEP 250, fine tuning logic is implemented. At STEP 250, it is assumed that the two QRS complexes are, for example, at least 200 msec apart. This assumed separation is greater than 300 beats-per-minute, which is an upper limit for a heart rate. Thus, the assumption does not result in eliminating a beat. Further, it is assumed at STEP 250 that, within a 1 sec window, there are not any two beats where one of the beats is ten or more times larger than the other. Accordingly, STEP 250 outputs fiducial points. In other words, STEP 250 outputs time points corresponding to high energy points in the ECG signal that may be used to detect beats.

Figure 7:
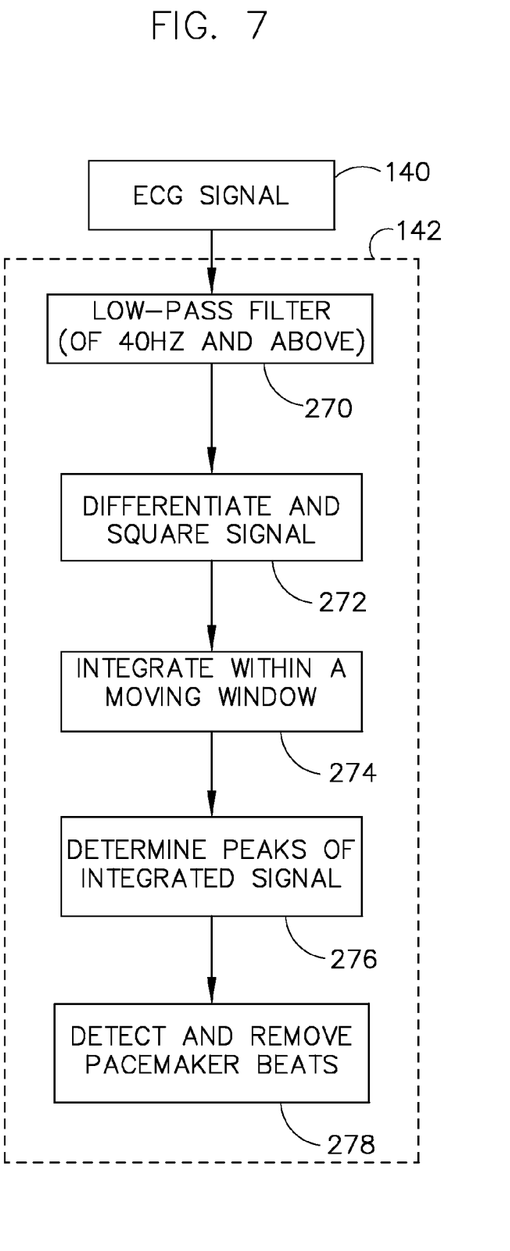
FIG. 7 is a flowchart depicting an embodiment of the removal of pacemaker noise shown in FIG. 3.

Referring now to FIG. 7, the logic of the pacemaker removal component at STEP 142 of FIG. 3 is shown according to an embodiment. As shown, the ECG lead signal 140 is allowed to pass through a low-pass filter at STEP 270 with a cut-off frequency of, for example forty hertz. The output of the low-pass filter at STEP 270 is then differentiated and squared at STEP 272. At STEP 274, the differentiated and squared signal is integrated within a moving window where the moving window may have an exemplary length of fifty msec. The peak of the integrated signal is then determined at STEP 276. The STEPs 270-276 allow for the narrow-width rectangle waves of pacemaker beats to be detected and removed at STEP 278.

A technical contribution for the disclosed method and apparatus is that it provides for a processor-implemented ECG lead signal quality determination and indication.

In accordance with one embodiment, an electrocardiogram (ECG) monitoring system is configured to determine an index that comprises a set of indicators, where each indicator is indicative of a level of signal quality in an ECG lead. Further, the ECG monitoring system assigns a first indicator from the set of indicators to a first ECG lead signal and communicates the first indicator to a user.

In accordance with another embodiment, a computer readable storage medium having stored thereon a computer program comprising instructions which when executed by a computing device cause the computing device to evaluate noise in a first electrocardiogram (ECG) lead signal, assign a first value from a quality index to the evaluated noise; and indicate the first value to a user.

In accordance with yet another embodiment, a method comprises determining a condition of an ECG lead, assigning a symbol indicative of the condition of the ECG lead; and assessing the alarm from the ECG system based on the symbol.

The invention has been described in terms of the preferred embodiment, and it is recognized that equivalents, alternatives, and modifications, aside from those expressly stated, are possible and within the scope of the appending claims.

What is claimed is:

1. An electrocardiogram (ECG) monitoring system configured to:
   determine noise from a first ECG lead signal, wherein the determination of the noise comprises subtracting a signal template corresponding to a noise-free cardiac signal from the first ECG lead signal;
   assign a signal quality indicator from a set of possible signal quality indicators to the first ECG lead signal based on the determined noise; and
   communicate the assigned signal quality indicator to a user.

2. The ECG monitoring system of claim 1 wherein the set of possible signal quality indicators is derived from one of a number scale, a color spectrum, and an audible signal.

3. The ECG monitoring system of claim 1 further configured to:
   assign an additional indicator from the set of possible signal quality indicators to multiple ECG lead signals, wherein the additional indicator is indicative of an overall quality of the multiple ECG leads; and
   communicate the additional indicator to the user.

4. The ECG monitoring system of claim 1 further configured to remove a pacemaker-induced signal from the first ECG lead signal.

5. The ECG monitoring system of claim 1 wherein the determined noise is substantially free of single-subject normal ECG amplitude variance contributions.

6. The ECG monitoring system of claim 1 wherein the determined noise is substantially free of signal contributions from premature ventricular contractions and ventricular ectopic beats.

7. The ECG monitoring system of claim 1, wherein the determination of noise is configured to account for subject-to-subject variances.

8. The ECG monitoring system of claim 1 further configured to communicate to the user that a lead failure event is likely to occur based on the a trend associated with the assigned signal quality indicator.

9. The ECG monitoring system of claim 1 further configured to determine that an alarm generated by the ECG monitoring system is a false alarm, wherein the determination that the alarm is a false alarm is based on the assigned signal quality indicator.

10. The ECG monitoring system of claim 1 wherein the signal template comprises a plurality of beat templates.

11. The ECG monitoring system of claim 10 wherein the plurality of beat templates are substantially free of artifact-causing noise.

12. The ECG monitoring system of claim 1 wherein the determination of the noise comprises determining fiducial points of the first ECG lead signal.

13. The ECG monitoring system of claim 12 wherein the determination of the noise comprises aligning the signal template with the first ECG lead signal using the determined fiducial points.

14. The ECG monitoring system of claim 1 wherein the assignment of the assigned signal quality indicator is based on analyzing the determined noise with an exponential threshold function nonlinearity.

15. An electrocardiogram (ECG) monitoring system configured to:
   determine noise from a first ECG lead signal in two or more frequency segments, where the determination of the noise from the first ECG lead signal in at least one frequency segment comprises subtracting a noise-free signal template corresponding to a cardiac signal from the first ECG lead signal in the at least one frequency segment;
   assign a first indicator from a set of possible signal quality indicators to the first ECG lead signal, wherein the assignment of the first indicator is based on the determined noise from all frequency segments; and
   communicate the first indicator to a user.

16. The ECG monitoring system of claim 15 wherein the signal template comprises a plurality of beat templates.

17. The ECG monitoring system of claim 16 wherein the plurality of beat templates are substantially free of artifact-causing noise.

18. The ECG monitoring system of claim 15 wherein the two or more frequency segments comprise at least an in-band frequency segment between approximately 0.7 and 40 Hz.

19. The ECG monitoring system of claim 15 wherein the assignment of the first indicator is based on analyzing the determined noise from the first ECG lead signal in at least one frequency segment with an exponential threshold function nonlinearity.

20. The ECG monitoring system of claim 15 wherein the assignment of the first indicator is based on a weighted average value of the determined noise from all frequency segments.

* * * * *

UNITED STATES PATENT AND TRADEMARK OFFICE
CERTIFICATE OF CORRECTION

| | | |
|---|---|---|
| PATENT NO. | : 8,805,482 B2 | Page 1 of 1 |
| APPLICATION NO. | : 12/180616 | |
| DATED | : August 12, 2014 | |
| INVENTOR(S) | : Sitzman et al. | |

It is certified that error appears in the above-identified patent and that said Letters Patent is hereby corrected as shown below:

In the Specification

In Column 10, Line 61, delete "STEPs 152-156" and insert -- STEPs 150-154 --, therefor.

In Column 11, Line 17, delete "fiducial points 140" and insert -- fiducial points --, therefor.

In Column 13, Line 47, delete "technique 176" and insert -- technique --, therefor.

In the Claims

In Column 15, Line 48, in Claim 8, delete "on the a" and insert -- on a --, therefor.

Signed and Sealed this
Twenty-fourth Day of February, 2015

Michelle K. Lee
*Deputy Director of the United States Patent and Trademark Office*